United States Patent
Zhu et al.

(10) Patent No.: US 6,505,071 B1
(45) Date of Patent: Jan. 7, 2003

(54) CARDIAC MANAGEMENT DEVICE WITH CAPABILITY OF NOISE DETECTION IN AUTOMATIC CAPTURE VERIFICATION

(75) Inventors: Qingsheng Zhu, Little Canada, MN (US); Michael Lyden, Shoreview, MN (US); Scott Freeberg, Birchwood Village, MN (US); Laura Mepham, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/461,976

(22) Filed: Dec. 15, 1999

(51) Int. Cl.[7] .................................................. A61N 1/18
(52) U.S. Cl. ........................................................ 607/28
(58) Field of Search .............................. 607/4, 7, 8, 9, 607/11, 27, 28

(56) References Cited

U.S. PATENT DOCUMENTS

| | | | | |
|---|---|---|---|---|
| 5,010,887 A | * | 4/1991 | Thronander | 128/696 |
| 5,522,860 A | * | 6/1996 | Molin et al. | 607/20 |
| 5,861,008 A | * | 1/1999 | Obel et al. | 607/11 |
| 6,029,086 A | * | 2/2000 | Kim et al. | 607/9 |

* cited by examiner

Primary Examiner—Jeffrey R. Jastrzab
Assistant Examiner—Frances P. Oropeza
(74) Attorney, Agent, or Firm—Nikolai & Mersereau, P.A.; C. G. Mersereau (57) ABSTRACT

An implantable cardiac rhythm management device operable in an autothreshold or autocapture verification mode, wherein the rhythm management device is capable of detecting noise that affects signal characteristics of a sensed intracardial evoked response electrogram signal. The device includes a noise detection circuit that determines whether a minimum peak timing occurs during a predetermined time following delivery of a stimulation pulse. If a minimum peak timing occurs during the predetermined time following delivery of the stimulation pulse, then significant amounts of noise affecting the signal characteristics of the electrocardiogram signal is assumed.

40 Claims, 6 Drawing Sheets

CARDIAC MANAGEMENT DEVICE WITH CAPABILITY OF NOISE DETECTION IN AUTOMATIC CAPTURE VERIFICATION

I. FIELD OF THE INVENTION

This invention relates generally to an implantable cardiac rhythm management device that may operate in an auto-threshold or autocapture verification mode, wherein the rhythm management device is capable of detecting noise that affects signal characteristics of a sensed electrocardiogram signal. The presence of noise in an electrocardiogram signal occurring in, for example, a capture detection window may adversely affect the ability of the device to respond to patient needs.

II. BACKGROUND OF THE INVENTION

Regardless of the type of cardiac rhythm management device that is employed, all operate to stimulate excitable heart tissue cells adjacent to the electrode of the lead coupled to the rhythm management device. Response to myocardial stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is approximately equal to the concentration of potassium ions inside the cell membrane. However, the selective permeability also retains other negative particles within the cell membrane such that the inside of the cell membrane is negatively charged with respect to the outside when the cell is at rest.

When a stimulus is applied tq the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibrils of the cell membrane. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is re-polarized with a negative charge within the cell membrane. This causes the cell membrane to relax and return to the fully extended state, referred to as diastole.

In a normal heart, the sino-atrial (SA) node initiates the myocardial stimulation described above. The SA node comprises a bundle of unique cells disposed within the roof of the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding a trial muscle cells such that the depolarization of the SA node cells causes the adjacent a trial muscle cells to depolarize. This results in a trial systole wherein the atria contract to empty and fill blood into the ventricles. The a trial depolarization from the SA node is detected by the atrioventricular (AV) node which, in turn, communicates the depolarization impulse into the ventricles via the Bundle of His and Purkinje fibers following a brief conduction delay.

In this fashion, ventricular systole lags behind atrial systole such that the blood from the ventricles is pumped through the body and lungs after being filled by the atria. Atrial and ventricular diastole follow wherein the myocardium is repolarized and the heart muscle relaxes in preparation for the next cardiac cycle. It is when this system fails or functions abnormally that a cardiac rhythm management device may be needed to deliver an electronic pacing stimulus to the heart so as to maintain proper heart rate and synchronization of the filling and contraction of the a trial and ventricular chambers of the heart.

The success of a cardiac rhythm management device in causing a depolarization or evoking a response hinges on whether the energy of the pacing stimulus as delivered to the myocardium exceeds a threshold value. This threshold value, referred to as the capture threshold, represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. If, on the other hand, the energy of the pacing stimulus exceeds the capture threshold, then the permeability of the myocardial cells will be altered such that depolarization will result.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at a level higher than necessary to effect capture. This can be verified by lowering the stimulation energy level and monitoring for loss of capture at the new energy level.

The ability to detect capture in a cardiac rhythm management device is extremely desirable in that delivering stimulation pulses having energy far in excess of the patient's capture threshold is wasteful of the cardiac rhythm management device's limited power supply. In order to minimize current drain on the power supply, it is desirable to automatically adjust the cardiac rhythm management device such that the amount of stimulation energy delivered to the myocardium is maintained at the lowest level that will reliably capture the heart. To accoimplish this, a processes known as "capture verification" and "autothreshold" may be performed wherein; the cardiac rhythm management device monitors to determine whether an evoked response or depolarization occurs in the heart following the delivery of each pacing stimulus pulse. The occurrence of noise during the autothreshold or autocapture mode may lead to an improper conclusion related to capture or non-capture.

Obel et al. in U.S. Pat. No. 5,861,008 apparently describes a heart-simulating device that measures the amplitude of noise and if a predetermined number of noise detections exceeding a predetermined amplitudes (detected at a predetermined frequency) then the device assumes that the noise is significant and adjusts accordingly. In some instances the amplitude of noise may not be sufficient or the frequency may not be enough such that the device described by Obel et al. adjusts accordingly, while in actuality the noise may have significant impact on the accuracy of evoked response determination. Hence, there is a need for a cardiac rhythm management device capable of detecting noise independent of the amplitude of noise or the frequency of occurrence of noise. These and numerous other disadvantages of the prior art necessitates the need for the method and apparatus provided by the present invention.

SUMMARY OF THE INVENTION

The present invention provides for a cardiac rhythm management device and method capable of detecting noise, wherein the device is operable in either a unipolar or bipolar sensing mode. In the past, during unipolar sensing, the presence of noise has adversely affected the ability of conventional rhythm management devices to accurately identify an evoked response to a stimulation pulse. The device of the present invention provides for unipolar sensing during either an autothreshold or capture verification mode, wherein the presence of noise affecting the signal characteristics of an electrocardiogram signal is identified during either mode. The cardiac rhythm management device may be electrically coupled to one or more known suitable leads having pacing/sensing electrodes coupled thereto.

Without limitation, the cardiac rhythm management device of the present invention includes a power supply, pulse generator that generates stimulation pulses, and controller coupled to pacing/sensing leads to receive sensed electrocardiogram signals (IEGM signals). The controller is electrically coupled to the pulse generator and controls delivery of the stimulation pulses to the heart. The controller also controls detection of intrinsic and evoked responses and may operate in an autocapture or autothreshold mode. A noise detection circuit of the controller allows for detection of noise affecting the signal characteristics of the IEGM signal.

The controller may be in any of several forms including a dedicated state device or a microprocessor with code, and may include ROM memory for storing programs to be executed by the controller and RAM memory for storing operands used in carrying out the computations by the controller. Those skilled in the art will appreciate that stimulation circuitry, sensing circuitry, timing circuitry, and wave detection circuitry among others may all be included within the controller. The controller and components contained therein or coupled thereto detect and distinguish cardiac depolarization deflections and noise deflections from the electrocardiogram signal. A peak detector, for example, may be utilized to determine the amplitudes of the cardiac depolarization deflections and artifact deflections.

Following delivery of a stimulation pulse, noise affecting signal characteristics of the electrocardiogram signal is assumed or determined if a minimum peak timing (Min T or tmin) is detected occurring during a predetermined period of time following delivery of a stimulation pulse. The predetermined period of time begins after a predetermined refractory period and more specifically may occur within an evoked response detection window controlled by the controller. Without limitation, in the preferred embodiment the refractory period ranges between 3–15 msec. and the predetermined noise detection period of time following the pace is between 20–55 msec. in length.

In use, the controller controls delivery of a stimulation to a patient's heart. An electrocardiogram signal from the patient's heart is sensed and the controller determines the time at which a minimum peak occurs following delivery of the stimulation pulse. If the time of the minimum peak occurs during a predetermined period of time following delivery of the stimulation pulse, then noise affecting the electrocardiogram signal is determined or assumed. During autocapture verification or autothreshold, the predetermined period of time is set to begin after expiration of a predetermined refractory period. Further, the predetermined period of time may be set to occur within an evoked response detection window controlled by the controller. During a capture verification mode, a backup stimulation is delivered and the capture verification stimulation mode is abandoned if noise is detected. During the autothreshold stimulation mode, a current stimulation amplitude of the stimulation pulse is maintained during the autothreshold stimulation mode if noise is detected. The autothreshold stimulation mode is terminated if detection of noise persists.

DESCRIPTION OF THE DRAWINGS

The accompanying drawings include the following Figures in which like numerals in the several views refer to corresponding parts.

DESCRIPTION OF THE INVENTION

The present invention represents broadly applicable improvements to detecting noise occurring during an evoked response detection sequence. The embodiments detailed herein are intended to be taken as representative or exemplary of those in which the improvements of the invention may be incorporated and are not intended to be limiting.

Figure 1:
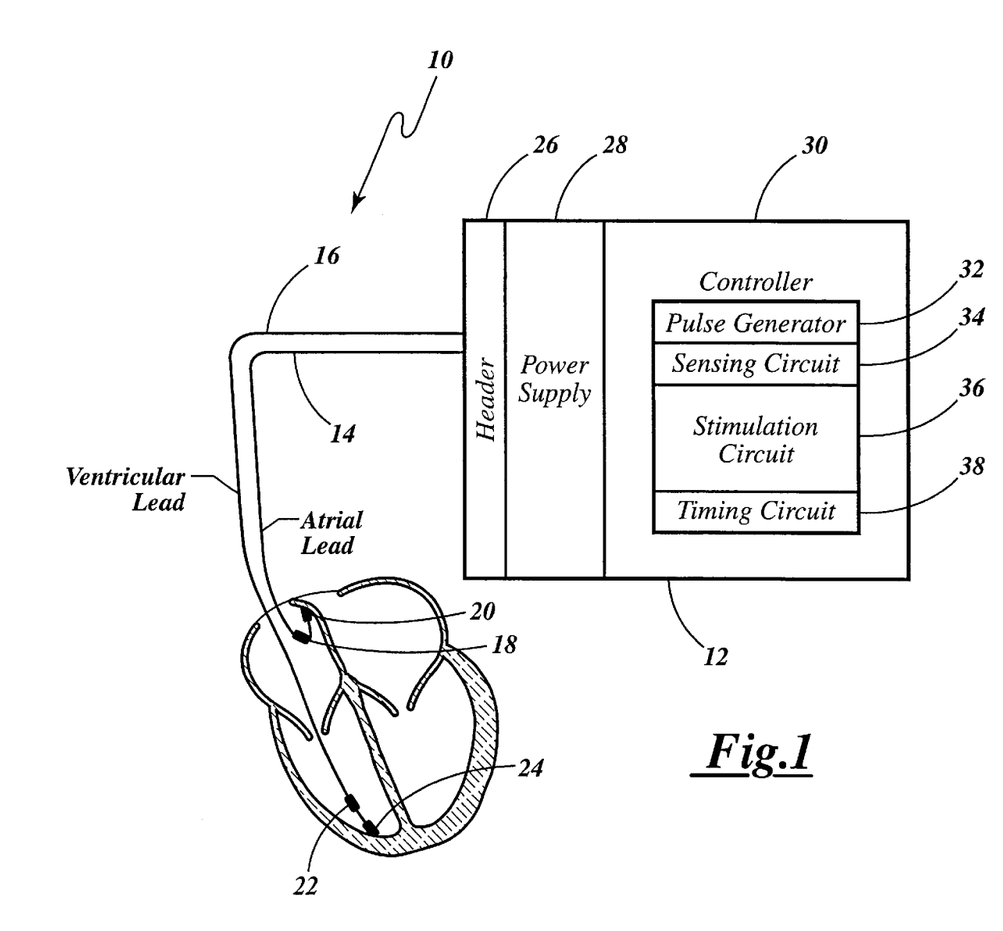
FIG. 1 is a block diagram depicting a cardiac rhythm management device in accordance with the present invention.

Referring first to FIG. 1, the cardiac rhythm management device 10 of the present invention is shown including a housing 12 coupled to a trial lead 14, and ventricular lead 16. The distal end of the a trial lead, shown positioned in the right atrium, includes electrodes 18 and 20. The distal end of the ventricular lead 16, shown positioned in the right ventricle, includes ventricular electrodes 22 and 24. The a trial lead 14 and ventricular lead 16 are engaged to header 26 and may be electrically coupled to the power supply 28 and controller 30 contained within the housing 12 in a known suitable fashion. Those skilled in the art will appreciate that other lead configurations of known suitable construction may be utilized dependent upon the particular desired stimulation and particular placement of the lead. Without limitation, the controller 30 includes a pulse generator 32, sensing circuit 34, stimulation circuit 36 and timing circuit 38. The pulse generator 32, sensing circuit 34, stimulation circuits 36, and timing circuit 38 of suitable known construction may be modified to include the noise detection circuit and protocol of the present invention as described below in greater detail.

Figure 2:
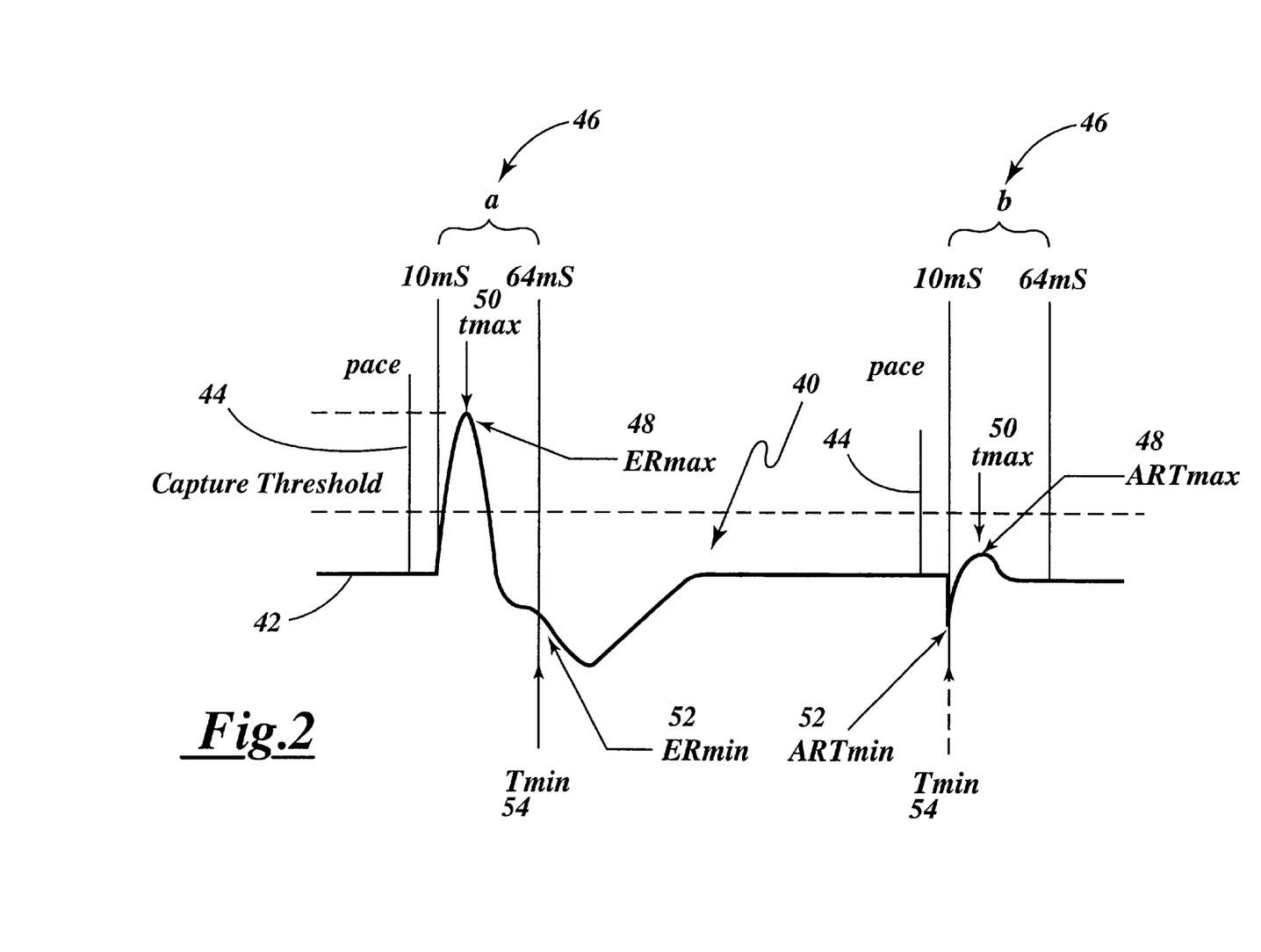
FIG. 2 is a plot of signal characteristics of an electrocardiogram signal having associated with a capture and non-capture event and the corresponding MinT during the evoked response interval.

FIG. 2 shows an electrocardiogram signal 40 resulting from unipolar sensing, wherein the signal 40 is shown in relation to various timing intervals of the controller and events sensed by the cardiac rhythm management system of the present invention. The baseline amplitude 42 of the electrocardiogram signal is represented by the horizontal line portion of the signal. When a stimulation pulse 44 is delivered to the patient's heart, if the heart is captured an evoked response is detected during detection window 46 (an evoked response is shown occurring in the first detection window or the detection window in the left portion of the figure labeled "a"). When a stimulation pulse 44 is delivered to the patient's heart, if non-capture results, stimulation artifact is detected during the detection window (stimulation artifact is shown occurring in the second detection window or the detection window in the right portion of the figure labeled "b"), however, the amplitude of the stimulation artifact does not exceed the capture threshold. Without limitation, the detection window 46 is shown as being the detection period between 10 msec–64 msec after the stimulation pulse 44 is delivered. A refractory period of 10 msec immediately precedes the evoked response detection window. During the detection window 46 four parameters may be identified: a maximum peak amplitude 48 (ERmax or ARTmax), maximum peak time 50 (tmax), minimum peak amplitude 52 (ERmin or ARTmin), and the minimum peak time 54 (tmin). The inventors have found that the occurrence or timing of the minimum peak 54 directly correlates with the presence or absence of noise that affects the signal characteristics of the electrocardiogram signal.

Figure 3:
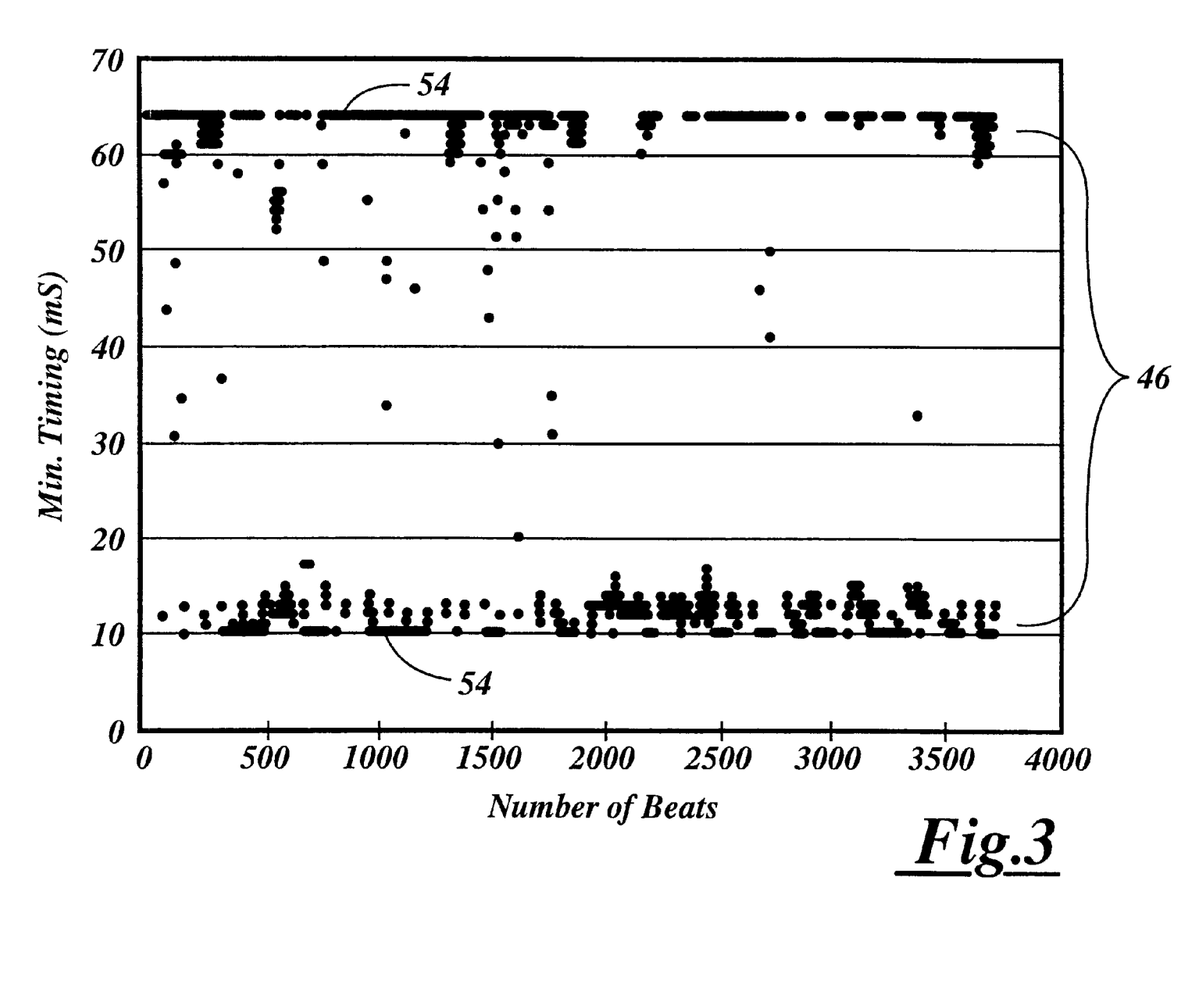
FIG. 3 is a graph showing the timing/occurrence of MinT over several beats and further shows a shift in MinT when noise is present.

FIG. 3 further illustrates this finding. As seen in FIG. 3, the minimum peak timing for either captured or non-captured events occurs approximately at 10 msec after a stimulation is delivered and again at approximately 64 msec after the stimulation is delivered (the extremes of the detection window 46). A significant amplitude of noise causes the timing of the detection of tmin 54 to shift, wherein a tmin 54 is detected somewhere in between the extremes or boundaries of the detection window. Thus, if a tmin is detected greater than 20 msec but less than 55 msec. significant noise has been determined and thus may be assumed.

Figure 4:
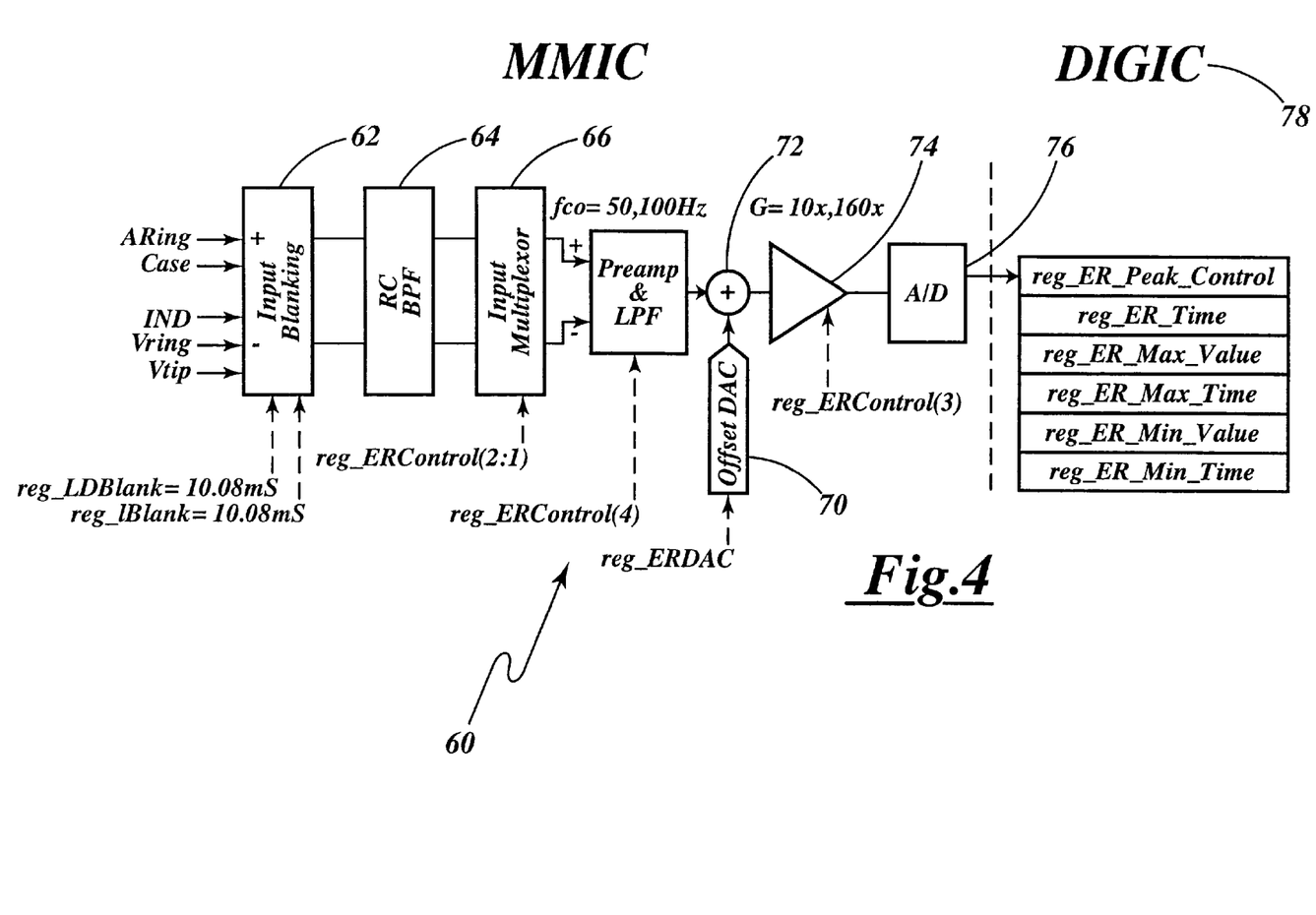
FIG. 4 is a schematic of an autocapture evoked response detection channel of the controller.

FIG. 4 shows the preferred embodiment of the autocapture evoked response detection channel of the controller 30. Without limitation, when ventricular autocapture is enabled, the paced evoked response is "sensed" to verify that the ventricular pace pulse has captured or depolarized the patient's ventricle. The evoked response detection channel 60 includes a Mixed Mode Integrated Circuit (MMIC) having an input blanking switch 62 electrically coupled to the electrodes of leads 14 and 16 of FIG. 1. The input blanking switches disconnect the sensing system from the lead system during the period of stimulation and the refractory period following stimulation. The timing of the opening and closing of these switches is controlled by registers identified as reg_LDBlank and reg_Iblank. Signals passing through the input blanking switch 62 passes through a wide bandpass filter 64 (RC BPF) of suitable known construction to attenuate high frequency signals from MV stimulus and other sources and to at least partially attenuate low frequency T-wave signals and DC offsets present on the lead. The filter may, for example without limitation, provide for a first order highpass pole at 8 Hz and a lowpass pole at 220 Hz. The filtered signal then passes through the input multiplexor 66. The wide bandpass filter 64 together with offset nulling eliminates the need for multiple high pass filters and avoids response "ringing" in the detected signal.

The multiplexor 66 allows for evoked response detection from several lead electrode combinations. Without limitation, in the preferred embodiment for ventricular autocapture, sensing occurs between the case and the ventricular tip electrode 24. The signal then passes through a preamplifier and lowpass filter 68 of suitable known construction, wherein the filter includes a cutoff frequency which, without limitation, may be set to 100 Hz for ventricular autocapture. The signal then passes through an offset digital to analog converter 70 and summing node 72 to nullify most offset. The signal then passes through a decimator stage 74 having gain control, to thereby reduce the evoked response channel's discrete time frequency sample rate. The signal then passes through an analog to digital converter 76 and the resulting signal is referred to as a digitized intracardial evoked response electrogram (the IEGM signal).

The Digital Integrated Circuit (DIGIC) 78 includes a hardware peak detection block that performs evoked response measurements following ventricular pace. When the evoked response min/max (ER Min/Max) is enabled, a peak detector measures both maximum and minimum evoked response values in relation to the time of occurrence within the measurement interval. As discussed above, the time at which the evoked response minimum is sensed is indicative of the presence or absence of significant noise in the IEGM signal.

Figure 5:
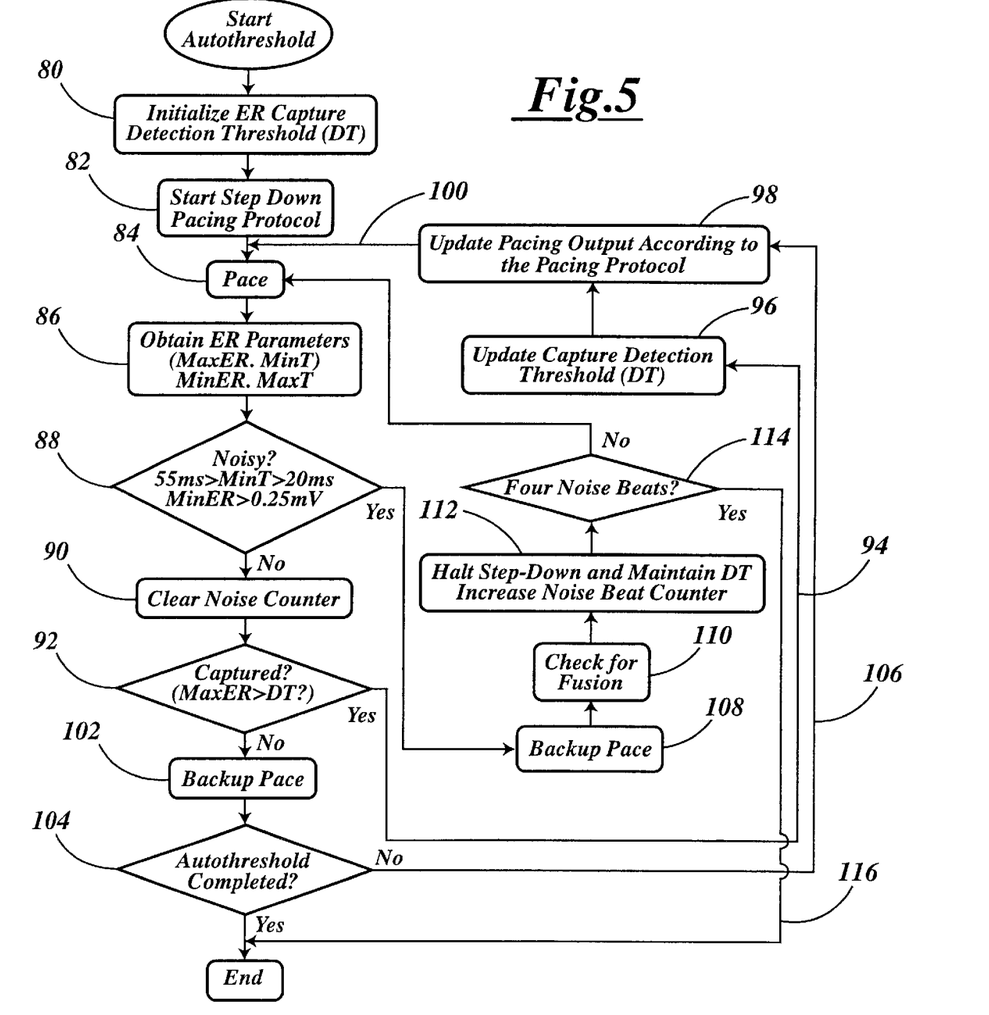
FIG. 5 is flowchart that illustrates generally the method of the present invention for detecting noise during an autothreshold stimulation mode.

Turning now to FIG. 5, the preferred embodiment of determining whether significant noise is present in the electrocardiogram signal during an Autothreshold mode will next be discussed. The controller 30 initializes the evoked response detection threshold (see block 80) and initiates a step down pacing protocol (see block 82) by delivering a stimulation pulse such as a pacing pulse to the heart (see block 84). In accordance with the method described above, the controller obtains the evoked response maximum, evoked response minimum and the timing associated with each (see block 86). The controller then determines whether the evoked response minimum occurs within a predetermined period of time, for example without limitation, between 20 msec and 55 msec. after the pacing stimulus is delivered, and also, wherein the MinER is greater than a preset amount, for example, 0.025 mV (see decision block 88). If the evoked response minimum does not occur during the predetermined period of time, then the noise counter is cleared (see block 90) and the controller determines whether the pacing stimulus is captured (see decision block 92). If the pacing stimulus is captured, the capture detection threshold is updated, the noise counter is cleared and the pacing output is updated according to the pacing protocol (see loop 94, block 96 and block 98 respectively) and pacing continues (see loop 100). If the pacing stimulus is not captured a backup pace is initiated (see block 102) and the controller determines whether autothreshold is complete (see decision block 104). If the autothreshold is not complete, the pacing output is updated according to the pacing protocol (see loop 106 and block 98) and pacing continues (see loop 100).

If the evoked response minimum occurs during the predetermined period of time (at decision block 88) then a backup pace is initiated (see block 108), the controller checks for fusion (see block 110) and the step down is terminated, the detection threshold is maintained and the noise counter is increased (see block 112). The controller then determines whether the noise counter has been increased a predetermined number of times (see decision block 114). If the noise counter has increased by a predetermined number of times then the autothreshold mode is terminated (see loop 116). If the noise counter has not been increased by the predetermined number of times, then pacing continues (see loop 118).

Figure 6:
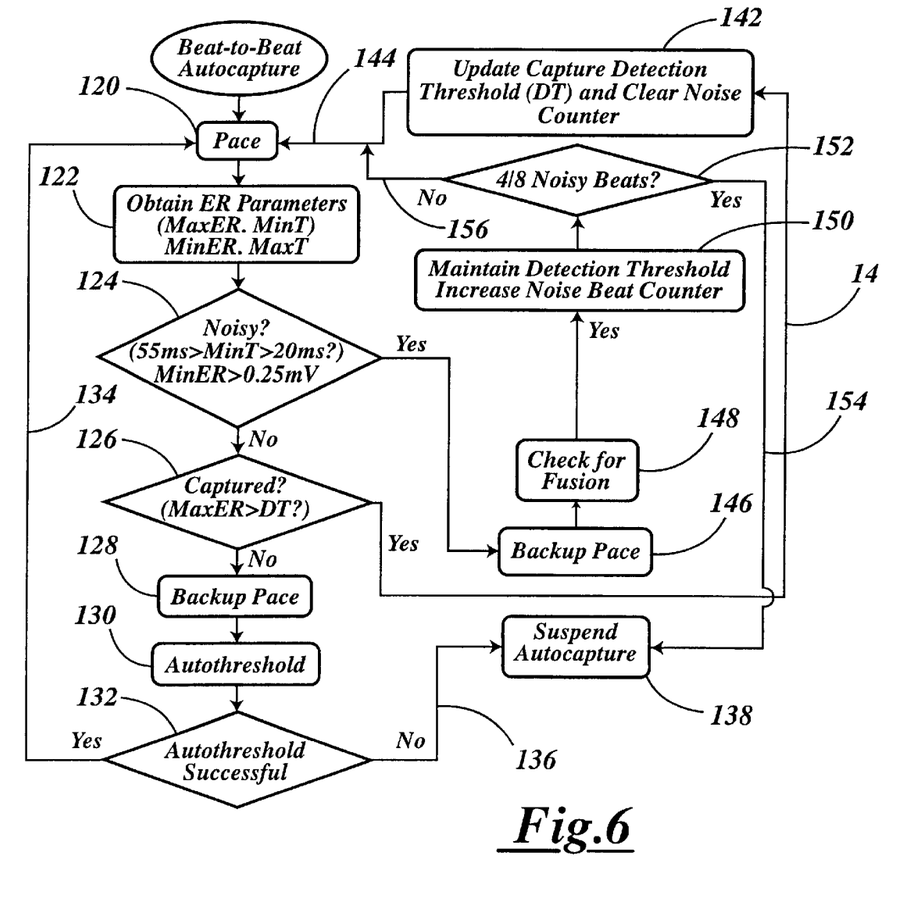
FIG. 6 is a flowchart that illustrates generally the method of the present invention for detecting noise during a capture verification mode.

In conjunction with FIG. 6, the preferred embodiment of determining whether significant noise is present in the IEGM signal during beat to beat an autocapture verification mode will next be presented. During beat to beat autocapture a stimulation pulse, for example a pacing stimulus, is delivered to the heart (see block 120) and the controller determines the resulting evoked response maximum, evoked response minimum and corresponding minimum peak timing (see block 124). The controller then determines whether the evoked response minimum occurs within a predetermined period of time, for example without limitation, between 20 msec and 55 msec. after the pacing stimulus is delivered (see decision block 124). If the evoked response minimum does not occur during the predetermined period of time, then the controller determines whether the stimulation pulse is captured, the evoked response maximum exceeds the detection threshold (see decision block 126). If the stimulation pulse is not captured, the controller initiates a backup pace (see block 128) and initiates the autothreshold mode (see block 130). If during the autothreshold mode the autothreshold is successfully updated (see decision block 132), then pacing continues (see loop 134). If the auto threshold is not updated then autocapture is suspended (see loop 136 and block 138). If the pacing stimulus captures the heart at decision block 126, then the capture detection threshold is updated and the noise counter is cleared (see loop 140 and block 142), and pacing continues at 120 (see loop 144).

If the evoked response minimum occurs during the predetermined period of time (at decision block 124) then a backup pace is initiated (see block 146), the controller checks for fusion (see block 148), the detection threshold is maintained and the noise counter is increased (see block 150). The controller then determines whether the noise counter has been increased a predetermined number of times (see decision block 152). In the preferred embodiment the controller determines whether noise is detected during four out of eight cycles. If the noise counter has increased by a predetermined number of times or ratio then autocapture is suspended (see loop 154.and block 138). If the noise counter has not been increased by the predetermined ratio, then pacing continues. (see loop 156 and block 120). Although the method of detecting noise of the present invention has been described with, respect to autocapture and autothreshold, those skilled in the art will appreciate that the method may equally apply for other stimulation modes.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device including:
   (a) a pulse generator that generates stimulation pulses;
   (b) a sensing circuit that senses an evoked response to one of the stimulation pulses; and
   (c) a noise detector coupled to said sensing circuit, wherein said noise detector includes a signal processor that monitors an evoked response electrogram signal (IEGM) signal and determines a time of minimum amplitude of the evoked response electrogram signal during a predetermined period of time following delivery of the stimulation pulse; and
   (d) wherein the time at which the evoked response electrogram signal minimum amplitude is sensed within the predetermined period of time determines the presence or absence of noise in the signal.

2. The rhythm management device as recited in claim 1, wherein the predetermined period of time begins after a predetermined refractory period corresponding to the stimulation pulse.

3. The rhythm management device as recited in claim 1, wherein the predetermined period of time occurs within an evoked response detection window controlled by the sensing circuit.

4. The rhythm management device as recited in claim 2, wherein said refractory period ranges between 3–15 msec.

5. The rhythm management device as recited in claim 1, wherein said predetermined period of time is between 20–55 msec in length.

6. The rhythm management device as recited in claim 1, wherein sensing of an evoked response electrogram (IEGM) signal is unipolar.

7. The rhythm management device as recited in claim 1, wherein a backup stimulation is delivered and a capture verification stimulation mode is abandoned when noise that affects signal characteristics of a sensed evoked response electrogram (IEGM) signal is detected.

8. The rhythm management device as recited in claim 7, wherein the capture verification stimulation mode is terminated when noise is detected occuring during at least half of several consecutive cardio cycles.

9. The rhythm management device as recited in claim 1, wherein automatic detection of noise occurs during an autothreshold stimulation mode.

10. The rhythm management device as recited in claim 1, wherein a stimulation amplitude is maintained during an autothreshold stimulation mode when noise affecting signal characteristics of a sensed evoked response electrogram (IEGM) signal is detected.

11. The rhythm management device as recited in claim 9, wherein the autothreshold stimulation mode is terminated when noise is detected during at least four consecutive cardiac cycles that affects signal characteristics of a sensed evoked response electrogram (IEGM) signal.

12. A cardiac rhythm management device including:
   (a) means for generating stimulation pulses;
   (b) sensing means for sensing an evoked response to one of the stimulation pulses;
   (c) sensing means for sensing an electrocardiogram signal;
   (d) noise detector means coupled to said sensing means, wherein said noise detector means includes a signal processor means that monitors an evoked response electrogram (IEGM) signal and for determining a minimum amplitude of the evoked response electrogram (IEGM) signal during a predetermined period of time following delivery of the stimulation pulse; and
   (e) wherein the time at which the evoked response elecrogram signal minimum amplitude is sensed within the predetermined period of time determines the presence or absence of noise in the signal.

13. The rhythm management device as recited in claim 12, wherein the predetermined period of time begins after a predetermined refractory period.

14. The rhythm management device as recited in claim 12, wherein the predetermined period of time occurs within an evoked response detection window controlled by the sensing means.

15. The rhythm management device as recited in claim 13, wherein said refractory period ranges between 3–15 msec.

16. The rhythm management device is recited in claim 12, wherein said predetermined period of time is between 20–55 msec in length.

17. The rhythm management device as recited in claim 12, wherein sensing of the evoked response electrogram (IEGM) signal is unipolar.

18. The rhythm management device as recited in claim 12, wherein a backup stimulation is delivered and a capture verification stimulation mode is abandoned when noise that affects signal characteristics of a sensed electrocardiogram signal is detected.

19. The rhythm management device as recited in claim 17, wherein a capture verification stimulation mode is terminated when noise is detected occurring during at least half of several consecutive cardiac cycles.

20. The rhythm management device as recited in claim 12, wherein automatic detection of noise occurs during an autothreshold stimulation mode.

21. The rhythm management device as recited in claim 12, wherein a stimulation amplitude is maintained during an autothreshold stimulation mode when noise affecting signal characteristics of a sensed electrocardiogram signal is detected.

22. The rhythm management device as recited in claim 20, wherein autothreshold stimulation mode is terminated when noise is detected during at least four consecutive cardiac cycles that affects signal characteristics of a sensed electrocardiogram signal.

23. An implantable cardiac rhythm management device operable in an automatic mode for detecting noise that affects the signal characteristics of an electrocardiogram signal, said rhythm management device including:

(a) a pulse generator that generates stimulation pulses;

(b) a controller having a timing circuit, said controller controls delivery of said stimulation pulses;

(c) electrodes designed to be positioned within a patient's heart and electrically connected to said controller, wherein stimulation pulses and electrocardiogram signals conduct through said electrodes;

(d) a noise detection circuit electrically coupled to said electrodes, wherein noise, affecting signal characteristics of the electrocardiogram signal, is detected if a time of minimum amplitude is detected by said noise detection circuit during a predetermined period of time following delivery of a stimulation pulse; and (e) an electrocardiogram detecting circuit electrically coupled to said electrode for sensing electrocardiogram signals.

24. The noise detection circuit of the rhythm management device is recited in claim 23, wherein said predetermined period of time begins after a predetermined refractory period controlled by said controller.

25. The noise detection circuit of the rhythm management device as recited in claim 23, wherein the predetermined period of time occurs within an evoked response detection window controlled by said controller.

26. The noise detection circuit of the rhythm management device as recited in claim 24, wherein said refractory period ranges between 3–5 msec.

27. The noise detection circuit of the rhythm management device as recited in claim 23, wherein said predetermined period of time is between 20–55 msec in length.

28. The noise detection circuit of the rhythm management device as recited in claim 23, wherein said circuit for sensing electrocardiogram signals is unipolar.

29. A method for detecting noise in a sensed electrocardiogram signal, said method comprising the steps of:

(a) delivering a stimulation pulse to a patient's heart;

(b) sensing an electrocardiogram signal responsive to the stimulation pulse;

(c) determining a minimum peak and timing thereof of the electrocardiogram signal following delivery of the stimulation pulse; and (d) determining the presence of noise in the electrocardiogram signal if minimum peak timing occurs during a predetermined period of time following delivery of the stimulation pulse.

30. The method according to claim 29, wherein the predetermined period of time is set to begin after a predetermined refractory period controlled by a controller.

31. The method according to claim 29, wherein the predetermined period of time is set to occur within a evoked response detection window controlled by a controller.

32. The method according to claim 29, wherein said predetermined period ranges between 3–15 msec.

33. The method according to claim 29, wherein said predetermined period of time is between 20–55 msec in length.

34. The method according to claim 29, wherein sensing the electrocardiogram signal is unipolar.

35. The method according to claim 29, wherein automatic detection of noise occurs during a capture verification stimulation mode.

36. The method according to claim 35, wherein a backup stimulation is delivered and the capture verification stimulation mode is abandoned when noise is detected that affects signal characteristics of an electrocardiogram signal sensed in step (b).

37. The method according to claim 35, wherein the capture verification stimulation mode is terminated when noise is detected occurring during at least half of several consecutive cardiac cycles.

38. The method according to claim 29, wherein automatic detection of noise occurs during an autothreshold stimulation mode.

39. The method according to claim 38, wherein a current stimulation amplitude is maintained during the autothreshold stimulation mode when noise is detected that affects signal characteristics of an electrocardiogram signal sensed in step (b).

40. The method according to claim 38, wherein the autothreshold stimulation mode is terminated when noise is detected during at least four consecutive cardiac cycles that affects signal characteristics of an electrocardiogram signal sensed in step (b).

* * * * *